United States Patent [19]
Robinson et al.

[11] Patent Number: 5,474,180
[45] Date of Patent: Dec. 12, 1995

[54] CONTAINER ASSEMBLY FOR TRANSPORT AND DISPOSAL OF MEDICAL MATERIALS

[75] Inventors: David A. Robinson, Bountiful; Brad C. Robinson, North Salt Lake; Kenneth L. Failor, Riverton, all of Utah

[73] Assignee: Specialized Health Products, Inc., Bountiful, Utah

[21] Appl. No.: 294,533

[22] Filed: Aug. 23, 1994

Related U.S. Application Data

[63] Continuation-in-part of Ser. No. 207,480, Mar. 7, 1994, abandoned.

[51] Int. Cl.⁶ ............................................. B65D 85/20
[52] U.S. Cl. ............................................. 206/366; 206/370
[58] Field of Search ............................................. 206/363–370, 206/438; 220/908–910

[56] References Cited

U.S. PATENT DOCUMENTS

| | | | |
|---|---|---|---|
| 930,113 | 8/1909 | Adams . | |
| 1,045,607 | 11/1912 | Payne . | |
| 1,121,426 | 12/1914 | Walter | 229/154 |
| 1,580,104 | 4/1926 | Hasselmann . | |
| 1,697,359 | 1/1929 | Huffman . | |
| 1,820,804 | 8/1931 | Huffman . | |
| 2,226,215 | 12/1940 | Borah | 229/125.37 |
| 2,435,994 | 2/1948 | Zukeman | 206/43 |
| 2,962,155 | 11/1960 | Rusciano | 206/17.5 |
| 2,971,688 | 2/1961 | Akers | 229/38 |
| 2,990,059 | 6/1961 | Hitt | 206/63.2 |
| 3,080,087 | 3/1963 | Cloyd | 220/31 |
| 3,148,822 | 9/1964 | Yochum, Jr. | 229/45 |
| 3,494,536 | 2/1970 | Henry | 206/370 |
| 3,900,550 | 8/1975 | Oliver et al. | 264/320 |
| 3,979,016 | 9/1976 | Frater | 220/315 |
| 4,009,818 | 3/1977 | Rogers | 229/23 R |
| 4,037,754 | 7/1977 | Wilhelmi et al. | 220/254 |
| 4,040,419 | 8/1977 | Goldman | 128/215 |
| 4,106,621 | 8/1978 | Sorenson | 206/365 |
| 4,121,755 | 10/1978 | Meseke et al. | 229/38 |
| 4,149,578 | 4/1979 | Hickey | 150/0.5 |
| 4,212,415 | 7/1980 | Neely | 222/231 |
| 4,270,536 | 6/1981 | Lemelson | 128/218 |
| 4,273,123 | 6/1981 | Lemelson | 128/218 |
| 4,315,592 | 2/1982 | Smith | 229/38 |
| 4,328,904 | 5/1982 | Iverson | 220/256 |
| 4,375,849 | 3/1983 | Hanifl | 206/366 |
| 4,452,358 | 6/1984 | Simpson | 206/366 |
| 4,520,926 | 6/1985 | Nelson | 206/366 |
| 4,576,281 | 3/1986 | Kirksey | 206/370 |
| 4,600,112 | 7/1986 | Shillington et al. | 215/274 |
| 4,679,700 | 7/1987 | Tharrington et al. | 220/337 |
| 4,722,472 | 2/1988 | Bruno | 229/128 |
| 4,733,778 | 3/1988 | Boeckmann et al. | 206/332 |
| 4,804,090 | 2/1989 | Schuh et al. | 206/366 |
| 4,809,850 | 3/1989 | Laible et al. | 206/366 |
| 4,816,307 | 3/1989 | Honeycutt | 428/34.1 |
| 4,826,073 | 5/1989 | Bruno | 229/128 |
| 4,828,107 | 5/1989 | Spencer | 206/366 |
| 4,840,272 | 6/1989 | Goldman | 206/365 |
| 4,848,569 | 7/1989 | Leishman | 206/365 |

(List continued on next page.)

FOREIGN PATENT DOCUMENTS

| | | |
|---|---|---|
| 484294 | 5/1992 | European Pat. Off. . |
| WO89/01905 | 3/1989 | WIPO ............................................. B65D 83/10 |

OTHER PUBLICATIONS

Devon Product Brochure–Published 1991.
Devon Industries Product Brochure, Published 1993.

*Primary Examiner*—Jimmy G. Foster
*Attorney, Agent, or Firm*—Gale H. Thorne; Paul S. Evans

[57] ABSTRACT

A container assembly for transport and disposal of medical instruments is disclosed and claimed. The container assembly preferably has a container body and a lid for use with multiple-sized container bodies. The lid includes a self-closing biased flap and a cradle member for insertion of sharp medical instruments and other medical waste without contact by medical personnel during insertion into the container.

32 Claims, 7 Drawing Sheets

U.S. PATENT DOCUMENTS

| | | | |
|---|---|---|---|
| 4,874,103 | 10/1989 | Quisenberry et al. | 220/1 T |
| 4,890,733 | 1/1990 | Anderson | 206/365 |
| 4,900,500 | 2/1990 | Honeycutt | 264/263 |
| 4,903,832 | 2/1990 | Stewart | 206/366 |
| 4,930,631 | 6/1990 | Bruno | 206/366 |
| 4,936,449 | 6/1990 | Conard et al. | 206/366 |
| 4,946,064 | 8/1990 | VanCucha | 220/355 |
| 4,969,554 | 11/1990 | Sawaya | 206/370 |
| 4,979,616 | 12/1990 | Clanton | 206/364 |
| 4,982,843 | 1/1991 | Jones | 206/366 |
| 5,054,618 | 10/1991 | Kim | 206/605 |
| 5,080,251 | 1/1992 | Noack | 220/335 |
| 5,103,997 | 4/1992 | Shillington et al. | 220/481 |
| 5,107,990 | 4/1992 | Wicherski et al. | 206/366 |
| 5,117,997 | 6/1992 | Fink | 220/23.86 |
| 5,183,180 | 2/1993 | Hawkins | 220/908 |
| 5,184,720 | 2/1993 | Packer et al. | 206/366 |
| 5,193,740 | 3/1993 | Newborough et al. | 206/370 |
| 5,269,457 | 12/1993 | de la Fuente | 206/366 |
| 5,271,500 | 12/1993 | Szacon | 206/366 |
| 5,271,500 | 12/1993 | Szacon | 206/366 |

# 5,474,180

CONTAINER ASSEMBLY FOR TRANSPORT AND DISPOSAL OF MEDICAL MATERIALS

BACKGROUND OF THE INVENTION

This patent application is a continuation-in-part of U.S. patent application Ser. No. 08/207,480, filed on Mar. 7, 1994, now abandoned, the disclosure of which is specifically incorporated herein.

FIELD OF THE INVENTION

The present invention relates generally to a container assembly which is useful for both transport and disposal of sharp medical instruments and other medical materials.

THE PRESENT STATE OF THE ART

The possibility of exposure to AIDS or other life-threatening diseases by medical personnel disposing of used sharp medical instruments has created a crucial need for an improved container that provides better protection against contracting potentially deadly diseases. The term "sharps" refers to sharp medical instruments such as syringes, scalpels, lances, and the like.

Sharps containers have been developed to facilitate the disposal of used medical instruments. Used instruments may be contaminated by bodily fluids of patients, or for other reasons may require sanitary disposal. However, the typical sharps container requires medical personnel to handle the sharp instrument during insertion into the container. For example, some sharps containers have two biased flaps through which sharps are horizontally inserted by pressing downward on the sharp while forcing it into the container. As the container fills, medical personnel run the risk of being stabbed by a previously inserted needle.

Additionally, improvements in the ability to transport sharps and dispose of them in the same container would be desirable. New sharps are typically transported in one type of container and then disposed of in another container after the sharps are used.

SUMMARY OF INVENTION

The present invention seeks to resolve a number of the problems which have been experienced in the prior art, as identified above. More specifically, the apparatus and method of this invention constitute an important advance in the art of containers, as evidenced by the following objects and advantages realized by the invention over the prior art.

One object of the present invention is to preclude handling of items being disposed of by personnel during insertion into the container, thereby precluding contact with previously disposed sharps or other medical materials.

Yet another object of the present invention is to provide for interchangeable use of a lid with a plurality of container bodies.

Another object of the present invention is to provide a self-closing flap over the container opening.

Additionally, it is an object of the present invention to provide a means for locking the lid of the container in a closed position to make it tamper resistant.

A further object of the present invention is to provide a means for removal and disposal of syringe needles.

The container must also be disposable and made of nontoxic and incineratable materials, whereas the container may be incinerated and/or disposed of at a disposal site.

Additional objects and advantages of the invention will be apparent from the description which follows, or may be learned by the practice of the invention.

Briefly summarized, the foregoing objects are achieved by a container assembly which is utilized for both the transport of new sharps and the disposal of contaminated or used sharps.

The preferred embodiment comprises a lid and container assembly. The lid is designed to be interchangeable with a variety of different sized containers. The lid is also designed to be temporarily secured to the container while transporting new medical instruments. When using the container for disposal purposes, the lid may be permanently secured to the container.

The opening of the lid is relatively restricted, thereby allowing for the receipt of contaminated medical instruments and preventing removal of previously disposed instruments in the associated container. The lid includes an area for placement of a contaminated article wherein a person may then dispose of the article without touching the article presently being disposed of as well as previously disposed articles. Moreover, the lid prevents further handling of used items by medical personnel subsequent to disposal. The invention may also comprise a single container wherein the lid and container are formed as one.

Non-medical items may be utilized with the inventive lid and container assembly. For example, batteries, industrial items, chemical items, cosmetics and computer software may be transported in a container incorporating the present invention and then disposed of in the same container. Household items such as chlorine bleach, lye, soap, phosphates, ammonia, vinegar and alcohol may also be transported and then disposed of in the same container.

When used with medical or chemical products, the container assembly may also contain an absorbent pad and chemical agents for neutralizing the items. In addition, the inventive container assembly may be used for transport and storage of agricultural items and automotive parts. Soiled automotive parts may later be safely disposed of in the same container. Other uses for the container include transport and disposal of environmentally unsafe products such as coal and oil.

These and other features of the present invention can be best understood from the following specification and drawings, of which the following is a brief description.

BRIEF DESCRIPTION OF DRAWINGS

In order to more fully understand the manner in which the above-recited advantages and objects of the invention are obtained, a more particular description of the invention will be rendered by reference to specific embodiments thereof which are illustrated in the appended drawings. Understanding that these drawings depict only typical embodiments of the invention and are therefore not to be considered limiting of its scope, the presently preferred embodiments and the presently understood best mode of the invention will be described with additional detail through use of the accompanying drawings in which.

DETAILED DESCRIPTION OF THE PREFERRED EMBODIMENT

Figure 5:
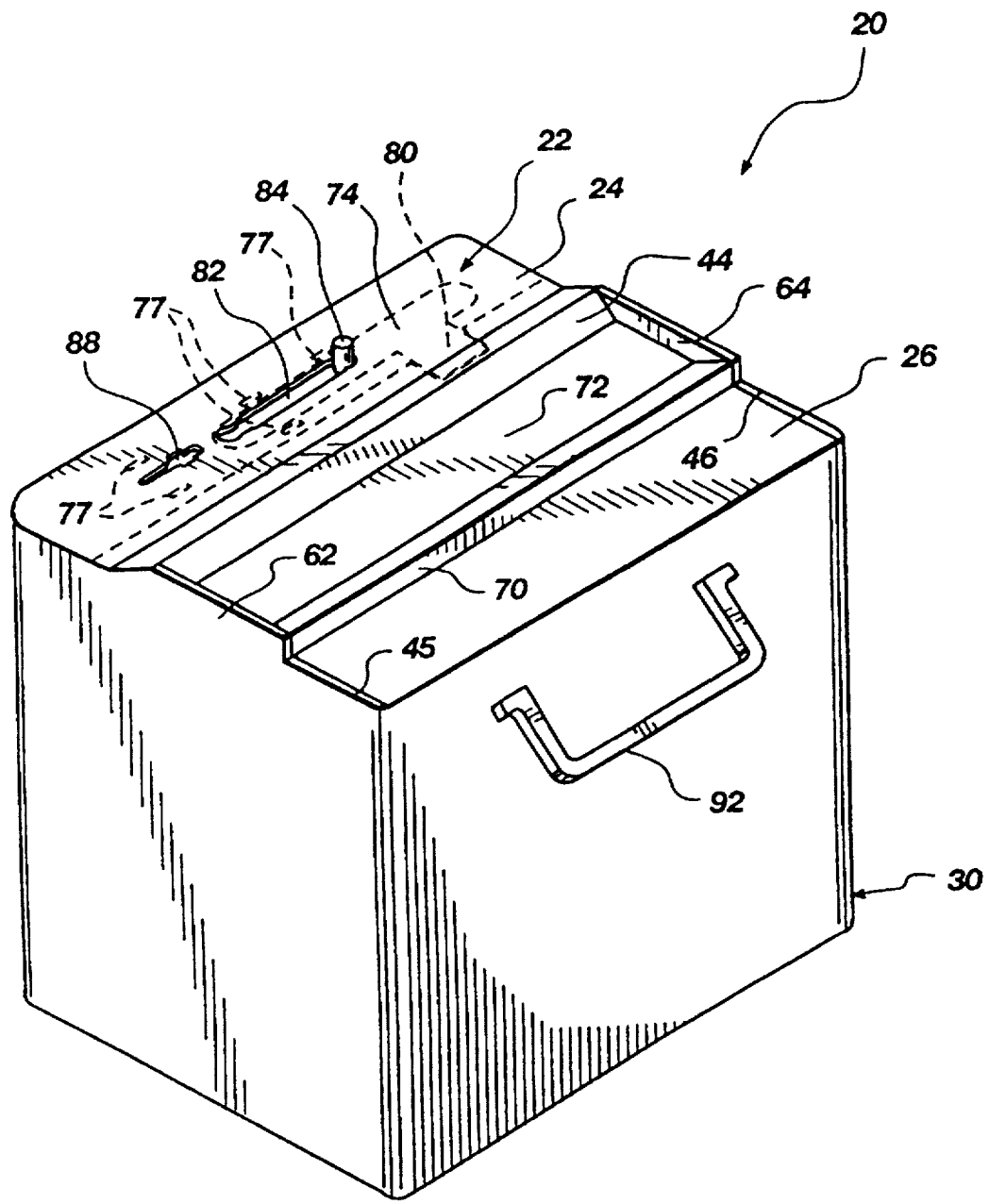
FIG. 5 is a perspective view showing the lid formed as part of the container assembly.
Figure 6:
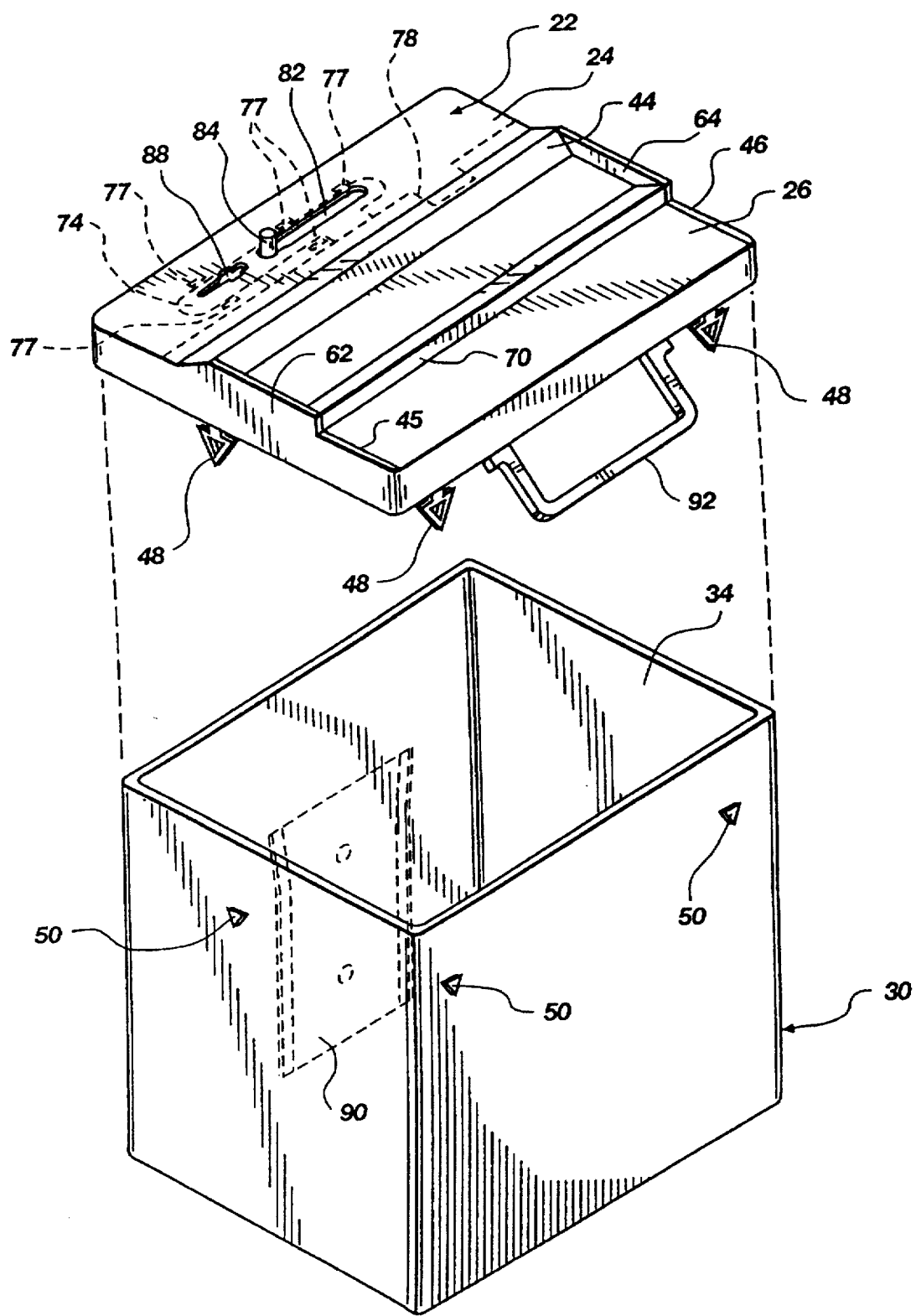
FIG. 6 is a perspective view showing an alternative means for securing the lid to the container by means of arrow tabs.
Figure 7:
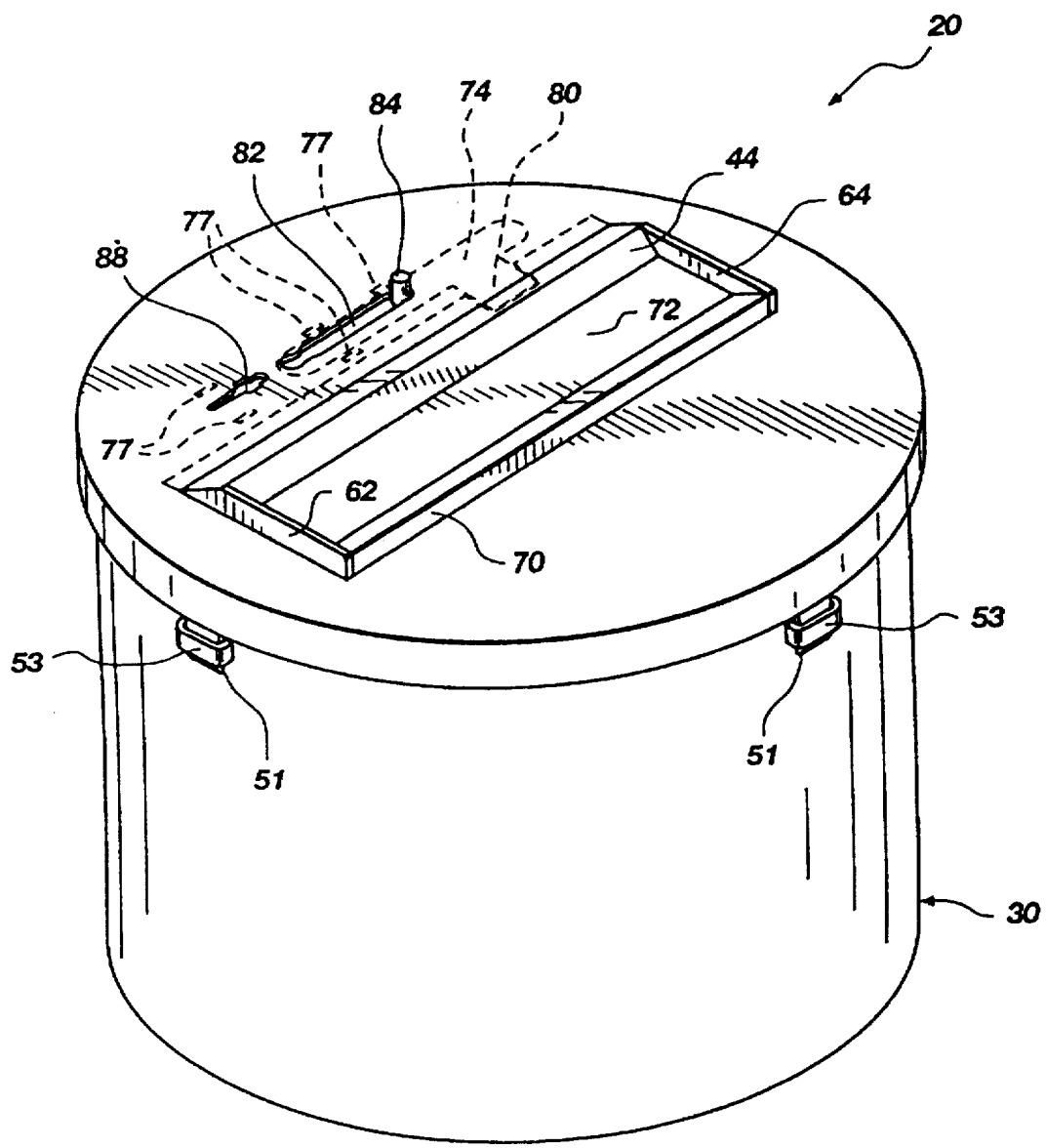
FIG. 7 is a perspective view showing a cylindrical container assembly.
Figure 8:
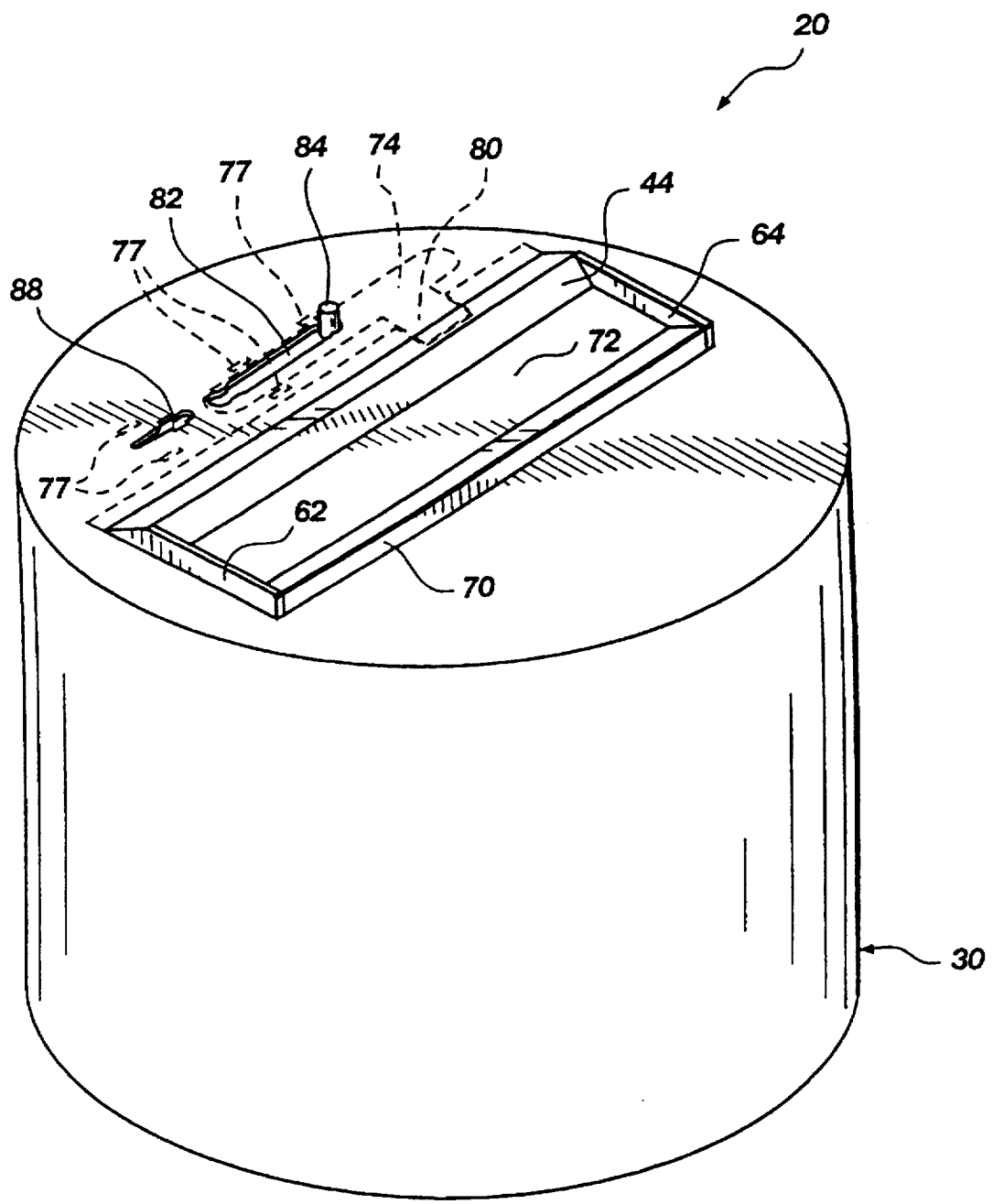
FIG. 8 is a perspective view showing the lid formed as part of the cylindrical container body.

Reference is now made to the drawings, wherein like numerals are used to denote like elements throughout. The container assembly of the present invention, generally designated 20, comprises a lid body 22, a self-closing biased flap 26, an opening 28, and a container body 30. The container body 30 defines a volume 32 and includes an opening 34. Although FIGS. 1–6 illustrate a rectangular shaped volume 32, one skilled in the art will recognize that many other shapes fall within the purview of this invention. For example, the container assembly may be square, spherical or cylindrical in shape as shown in FIGS. 7 and 8. Of course, manufacturing concerns are important in determining the shape of the volume 32. In the preferred embodiment, the lid body 22 is separate from the container body 30. The lid body 22 is adapted to be used with a plurality of container bodies 30. This design feature facilitates the manufacturing ease in which a variety of multiple-sized containers are produced for use with a one-size-fits-all container lid. However, the lid body 22 may also be formed as part of the container body 30 as shown in FIGS. 5 and 8. Each of these elements, as well as many others, will be discussed in greater detail hereafter.

The lid 22 and container body 30 are preferably constructed of a semi-rigid plastic or similar material which is lightweight, non-toxic, incineratable, inexpensive, easily manufactured, and sturdy. Size considerations may dictate that the container body 30 further comprise ribs to enhance structural integrity.

The biased flap 26 includes a first end 66 and a second end 68 wherein the biasing feature is accomplished by a living hinge 38 at the first end 66. A living hinge refers to hinged material having memory, such that when it is forcibly bent, it returns to its original position. The hinged material is typically notched along the living hinge. The biasing may also be accomplished by a spring interposed between the biased flap 26 and the container body 30.

The container assembly 20 also comprises a cradling means for insertion of medical instruments and waste into the container body 30 through the opening 28, wherein the cradling means has a floor 72 disposed on the biased flap 26. The cradling means is defined by an area surrounded by enclosure walls. A first enclosure wall 70 extends outwardly from the container body 30. The biased flap 26 has a first side 45 and a second side 46, wherein the first enclosure wall 70 extends from the first side 45 to the second side 46 of the biased flap 26 and is located between the first end 66 and the second end 68 of the biased flap 26. The second enclosure wall is defined by a combination of enclosure walls 44, 62, and 64. The second enclosure wall extends outwardly on the container body opening 34 and is defined by the perimeter of the container body opening 34 abutting the second end 68 of the biased flap 26 and the first side 45 and second side 46 of the biased flap 26 between the first enclosure wall 70 and the second end 68 of the biased flap 26, such that a cradling means floor 72 is defined by the area enclosed by the first and second enclosure walls. One skilled in the art will recognize that the enclosure walls may be constituted in a number of combinations of securement to the lid body 22 or container body 30. For example, enclosure wall 62 and enclosure wall 64 may be formed with first enclosure wall 70 on the biased flap 26. Alternatively, first enclosure wall 70, enclosure wall 62, and enclosure wall 64 may be formed as one part with enclosure wall 44 on the container body 30. The cradling means may also comprise a recessed area in the biased flap 26. For example, the biased flap 26 may step inwardly such that the sides of the container body 30 act as enclosure walls.

The container assembly also comprises a stopping means for maintaining the biased flap 26 in a closed position. Preferably, the stopping means comprises a second flap 24 affixed to the container body 30 at the opening 34 and extending towards the biased flap 26 such that the second flap 24 overlies a portion 36 of the biased flap 26. The biased flap 26 is biased against the second flap 24 by use of a living hinge 38. In this manner, the opening 28 is normally closed. In this embodiment, the second flap 24 also includes a first and second end 40 and 42, respectively. The second end 42 of the second flap 24 includes an enclosure wall 44 protruding in a direction normal to the second flap 24. The stopping means may also comprise one or more tabs positioned at the container opening 34 and overlying a portion of the second end 68, first side 45, or second side 46 of the biased flap 26.

The lid 22 is attached to the container body 30 by an attaching or securing means. In the preferred embodiment, the attaching means comprises a plurality of tabs 47 located on the perimeter of the lid 22. Each tab 47 includes a distal end at which is disposed a protruding edge 51 for engagement with a corresponding female slot 53 located on the container. Once the tab 47 is fully inserted through the female slot 53, the protruding edge 51 locks the tabs in place. Alternatively, hinged pull tabs hingedly secured to the lid may be utilized, as shown in FIG. 6. In this embodiment, each pull tab includes a female end 48 of an arrow lock for engagement with a corresponding male end 50 located on the container body 30. One skilled in the art will recognize that these methods serve as attaching or securing means, although other methods may be used which are equivalent and thus fall within the scope of this invention. For example, the securing means may comprise a tongue and groove configuration or other locking tab configurations typically found in lid and container assemblies. The attaching means may be continuous or intermittent around the perimeter of the container opening 34 and lid body 22.

In the preferred embodiment, the tabs 47 and slots 53 are not positioned symmetrically about the perimeter of the lid 22 so that the lid 22 can be rotated one-hundred and eighty degrees to avoid permanent securement during shipment of new medical instruments. Once the new medical instruments are removed, the lid 22 is then oriented for engagement of the tabs 47 into the corresponding slots 53 for permanent securement while using the container 30 for disposal purposes. Alternative securing means would similarly be misaligned for temporary and later permanent securement.

Figure 2:
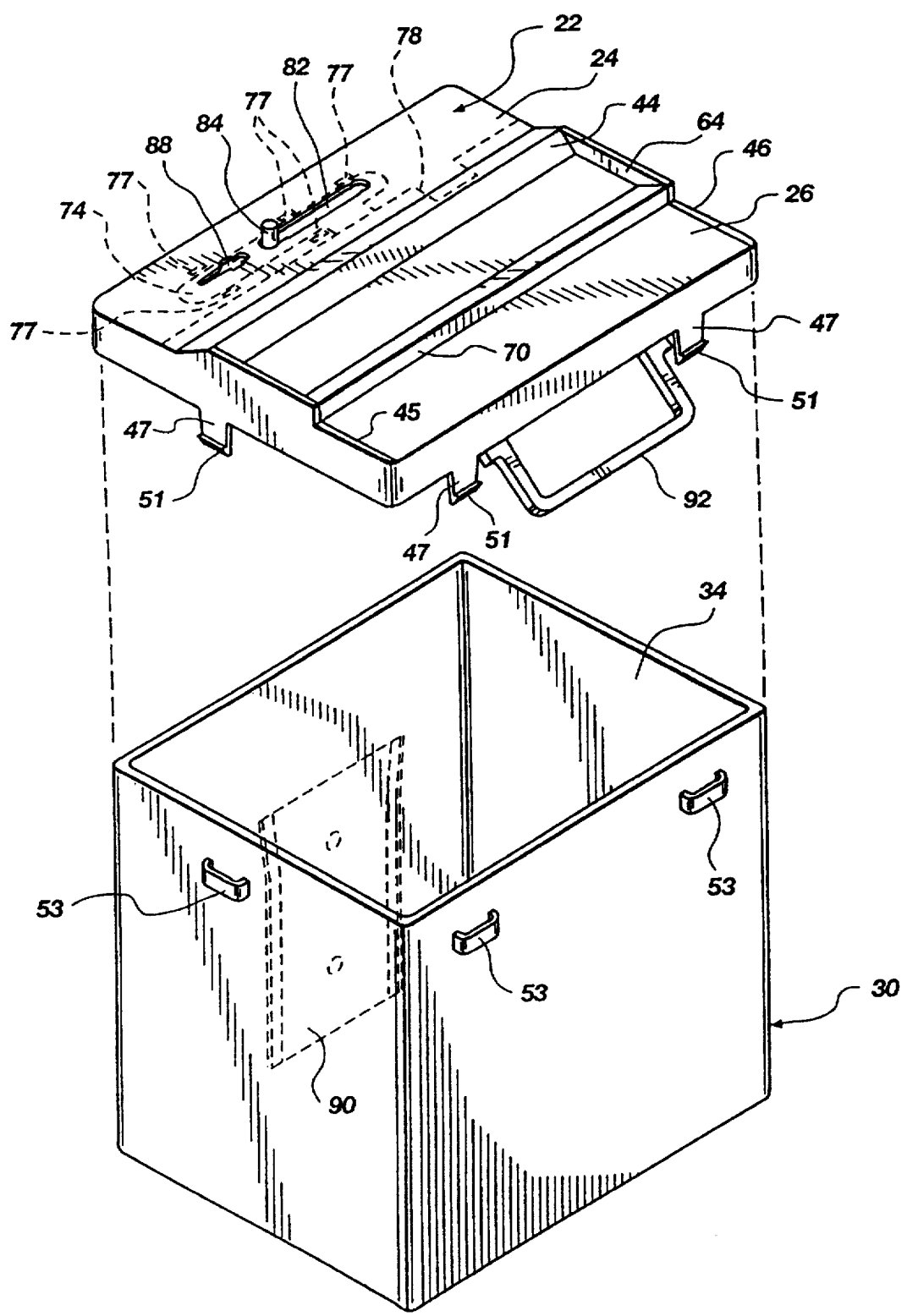
FIG. 2 is a perspective view showing the lid separate from the container.

The container assembly 20 further comprises a means for locking the biased flap 26 in a closed position. In the preferred embodiment the locking means comprises an elongated plate 74 slidably mounted to the underside 76 of the second flap 24. The plate 74 slides along tracks 77. The second end 68 of the biased flap 26 includes a notch 78 which is configured to match the outline of a tab 80 extending outwardly from the elongated plate 74. The profile of the tab 80 is slightly smaller than the notch 78 so that the biased flap 26 may be freely depressed while the locking means is in the open position. The closed position is defined by the plate 74 positioned such that the tab 80 is located adjacent to the notch 78, thereby preventing depression of the biased flap 26, as shown in FIG. 2. The second flap 24 also includes a slit 82 for slidable translation of a knob 84 attached to the plate 74 for positioning in an open, closed, or permanently closed position. The permanently closed position is defined by the knob 84 extended past a necked section 86 in the slit 82 of slightly smaller width than the knob 84.

Additionally, a strip of adhesive tape may be used as a method of sealing the second and biased flaps 24 and 26, respectively, together.

The container assembly 20 further comprises a means for extracting needles from a syringe. In the preferred embodiment, a tapered opening 88 located on the second flap 24 is used for extracting needles from a syringe. The needle is removed from the syringe by slidably engaging the needle base in the narrowest portion of the tapered opening 88 allowed and then twisting the syringe such that the threaded needle base dislodges from the syringe and falls into the volume 32. The means for extracting needles may also comprise multiple-sized openings, either separate or in series, which correspond to the geometry of the base of the needle such that when the needle base is inserted through the opening, the sides of the opening lockably fix the needle base for removal of the needle and insertion into the container assembly 20.

The container assembly 20 is also adapted to be mounted to a wall surface by means of a bracket 90 which is attached to the container body 30 and a corresponding adapter rigidly secured to the wall surface. For example, this adaptation of the container assembly 20 is advantageous in a hospital setting whereby a number of medical personnel may utilize the invention in a convenient and centralized locale.

The container assembly 20 for transporting and disposing of medical instruments is used as follows. When the container assembly 20 is used for transporting new medical instruments, the instruments are placed inside the container volume 32 with the lid 22 temporarily secured by orienting the tabs 47 and slots 53 in the misaligned position. When the container assembly 20 is used for disposal of used medical instruments, the lid 22 is permanently secured to the container 30 by orienting the tabs 47 and corresponding slots 53 in the aligned position such that the tabs 47 slide through the slots 53 and the protruding edges 51 lock the tabs 47 in place. The medical instruments desired to be disposed of are inserted into the container assembly 20 by placing the instruments on the floor 72 of the cradling means defined by the enclosure walls 44, 62, 64 and first enclosure wall 70, and then pressing downward on the biased flap in an area adjacent to the cradling means, thereby allowing the instruments to fall inside the volume 32 without contacting the instruments disposed of. Once the instruments are inserted, the danger of the instruments accidentally falling out or injuring someone are virtually eliminated. The lid 22 body of the container assembly 20 is then locked by sliding the knob 84 into the permanently locked position prior to transporting. A handle 92 attached to the container assembly 20 further facilitates its transportability.

In summary, the method and apparatus disclosed herein is a significant improvement from the present state of the containers for the sealed transport and disposal of medical instruments.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A container for use in transport and disposal of medical instruments, comprising:

a container body having an opening;

a self-closing biased flap connected to the container body for covering the opening;

a cradling means for insertion of medical instruments and waste into the container body through the opening, said cradling means comprising:

a first enclosure wall on the biased flap extending outwardly from the container body, said biased flap having a first side, a second side, a first end, and a second end, said first enclosure wall extending from the first side to the second side and located between the first end and second end of the biased flap;

a second enclosure wall on the container body opening extending outwardly and defined by the container body opening abutting the second end of the biased flap and the first side and second side of the biased flap between the first enclosure wall and second end of the biased flap; and a floor defined by an area on the biased flap enclosed by the first enclosure wall and the second enclosure wall.

2. A device as defined in claim 1, further comprising a stopping means for maintaining the biased flap in a closed position.

3. A device as defined in claim 2, further comprising a means for locking the biased flap in the closed position.

4. A device as defined in claim 3, wherein said stopping means comprises a second flap affixed to the container body at the opening and extending towards the biased flap, said second flap overlying a portion of the biased flap, said second flap including an underside and the biased flap having a second end extending towards the second flap, said second end of the biased flap including a notch, and the locking means comprising an elongated plate with an outwardly extending tab of a shape corresponding to the notch, said plate slidably mounted to the underside of the second flap, and the closed position defined by the plate positioned such that the tab is located adjacent to the notch on the biased flap, thereby preventing depression of the biased flap.

5. A device as defined in claim 4, wherein the second flap includes a slit for slidable translation of a knob adapted to be attached to the plate for positioning in an open, closed, or permanently closed position.

6. A device as defined in claim 5, wherein the open position is defined by the tab in alignment with the notch in the biased flap such that the biased flap may be depressed without interference of the tab.

7. A device as defined in claim 5, wherein the slit includes a necked section of slightly smaller width than the knob and the permanently closed position is defined by the knob extended beyond the necked section in the slit.

8. A device as defined in claim 3, further comprising means for extracting needles from a syringe.

9. A device as defined in claim 8, wherein said stopping means comprises a second flap affixed to the container body at the opening and extending towards the biased flap, said second flap overlying a portion of the biased flap, said second flap including an underside and the biased flap having a second end extending towards the second flap, said second end of the biased flap including a notch, and the locking means comprising an elongated plate with an outwardly extending tab of a shape corresponding to the notch, said plate slidably mounted to the underside of the second flap, and the closed position defined by the plate positioned such that the tab is located adjacent to the notch on the biased flap, thereby preventing depression of the biased flap.

10. A device as defined in claim 9, wherein the second flap includes a slit for slidable translation of a knob adapted to be attached to the plate for positioning in an open, closed, or permanently closed position.

11. A device as defined in claim 10, wherein the open position is defined by the tab in alignment with the notch in the biased flap such that the biased flap may be depressed without interference of the tab.

12. A device as defined in claim 10, wherein the slit includes a necked section of slightly smaller width than the knob and the permanently closed position is defined by the knob extended beyond the necked section in the slit.

13. A device as defined in claim 11, wherein said stopping means comprises a second flap affixed to the container body at the opening and extending towards the biased flap, said second flap overlying a portion of the biased flap, said second flap including an underside and the biased flap having a second end extending towards the second flap, said second end of the biased flap including a notch, and the locking means comprising an elongated plate with an outwardly extending tab of a shape corresponding to the notch, said plate slidably mounted to the underside of the second flap, and the closed position defined by the plate positioned such that the tab is located adjacent to the notch on the biased flap, thereby preventing depression of the biased flap.

14. A device as defined in claim 3, further comprising a stopping means for maintaining the biased flap in a closed position.

15. A device as defined in claim 14, further comprising a means for locking the biased flap in the closed position.

16. A device as defined in claim 15, further comprising means for extracting needles from a syringe.

17. A lid which attaches to containers for transport and disposal of medical instruments, comprising:
- a lid body for enclosing a volume within a container, said lid body having an opening;
- a self-closing biased flap connected to the lid body for covering the opening;
- means for attaching said lid body to said container; and
- cradling means for insertion of medical instruments and waste through the opening, said cradling means comprising:
  - a first enclosure wall on the biased flap extending outwardly from the lid body, said biased flap having a first side, a second side, a first end, and a second end, said first enclosure wall extending from the first side to the second side and located between the first end and second end of the biased flap;
  - a second enclosure wall on the lid body opening extending outwardly and defined by the lid body opening abutting the second end of the biased flap and the first side and second side of the biased flap between the first enclosure wall and second end of the biased flap; and
  - a floor defined by an area on the biased flap enclosed by the first enclosure wall and the second enclosure wall.

18. A device as defined in claim 17, further comprising a stopping means for maintaining the biased flap in a closed position.

19. A device as defined in claim 18, further comprising means for locking the biased flap in the closed position.

20. A device as defined in claim 19, wherein said stopping means comprises a second flap affixed to the container body at the opening and extending towards the biased flap, said second flap overlying a portion of the biased flap, said second flap including an underside and the biased flap having a second end extending towards the second flap, said second end of the biased flap including a notch, and the locking means comprising an elongated plate with an outwardly extending tab of a shape corresponding to the notch, said plate slidably mounted to the underside of the second flap, and the closed position defined by the plate positioned such that the tab is located adjacent to the notch on the biased flap, thereby preventing depression of the biased flap.

21. A device as defined in claim 20, wherein the second flap includes a slit for slidable translation of a knob adapted to be attached to the plate for positioning in an open, closed, or permanently closed position.

22. A device as defined in claim 21, wherein the open position is defined by the tab in alignment with the notch in the biased flap such that the biased flap may be depressed without interference of the tab.

23. A device as defined in claim 21, wherein the slit includes a necked section of slightly smaller width than the knob and the permanently closed position is defined by the knob extended beyond the necked section in the slit.

24. A device as defined in claim 19, further comprising means for extracting needles from a syringe.

25. A device as defined in claim 24, wherein said stopping means comprises a second flap affixed to the container body at the opening and extending towards the biased flap, said second flap overlying a portion of the biased flap, said second flap including an underside and the biased flap having a second end extending towards the second flap, said second end of the biased flap including a notch, and the locking means comprising an elongated plate with an outwardly extending tab of a shape corresponding to the notch, said plate slidably mounted to the underside of the second flap, and the closed position defined by the plate positioned such that the tab is located adjacent to the notch on the biased flap, thereby preventing depression of the biased flap.

26. A device as defined in claim 25, wherein the second flap includes a slit for slidable translation of a knob adapted to be attached to the plate for positioning in an open, closed, or permanently closed position.

27. A device as defined in claim 26, wherein the open position is defined by the tab in alignment with the notch in the biased flap such that the biased flap may be depressed without interference of the tab.

28. A device as defined in claim 26, wherein the slit includes a necked section of slightly smaller width than the knob and the permanently closed position is defined by the knob extended beyond the necked section in the slit.

29. A device as defined in claim 27, wherein said stopping means comprises a second flap affixed to the container body at the opening and extending towards the biased flap, said second flap overlying a portion of the biased flap, said second flap including an underside and the biased flap having a second end extending towards the second flap, said second end of the biased flap including a notch, and the locking means comprising an elongated plate with an outwardly extending tab of a shape corresponding to the notch, said plate slidably mounted to the underside of the second flap, and the closed position defined by the plate positioned such that the tab is located adjacent to the notch on the biased flap, thereby preventing depression of the biased flap.

30. A device as defined in claim 29, further comprising a stopping means for maintaining the biased flap in a closed position.

31. A device as defined in claim 30, further comprising means for locking the biased flap in the closed position.

32. A device as defined in claim 31, further comprising means for extracting needles from a syringe.

* * * * *

UNITED STATES PATENT AND TRADEMARK OFFICE
CERTIFICATE OF CORRECTION

PATENT NO.   : 5,474,180

DATED        : Dec. 12, 1995

INVENTOR(S)  : David A. Robinson et al

It is certified that error appears in the above-identified patent and that said Letters Patent is hereby corrected as shown below:

Columns 1-10 should be deleted, and substitute therefor columns 1-10, as shown on the attached pages.

Signed and Sealed this

Seventh Day of October, 1997

Attest:

BRUCE LEHMAN

*Attesting Officer*          *Commissioner of Patents and Trademarks*

CONTAINER ASSEMBLY FOR TRANSPORT AND DISPOSAL OF MEDICAL MATERIALS

BACKGROUND OF THE INVENTION

This patent application is a continuation-in-part of U.S. patent application Ser. No. 08/207,480, filed on Mar. 7, 1994, now abandoned, the disclosure of which is specifically incorporated herein.

FIELD OF THE INVENTION

The present invention relates generally to a container assembly which is useful for both transport and disposal of sharp medical instruments and other medical materials.

THE PRESENT STATE OF THE ART

The possibility of exposure to AIDS or other life-threatening diseases by medical personnel disposing of used sharp medical instruments has created a crucial need for an improved container that provides better protection against contracting potentially deadly diseases. The term "sharps" refers to sharp medical instruments such as syringes, scalpels, lances, and the like.

Sharps containers have been developed to facilitate the disposal of used medical instruments. Used instruments may be contaminated by bodily fluids of patients, or for other reasons may require sanitary disposal. However, the typical sharps container requires medical personnel to handle the sharp instrument during insertion into the container. For example, some sharps containers have two biased flaps through which sharps are horizontally inserted by pressing downward on the sharp while forcing it into the container. As the container fills, medical personnel run the risk of being stabbed by a previously inserted needle.

Additionally, improvements in the ability to transport sharps and dispose of them in the same container would be desirable. New sharps are typically transported in one type of container and then disposed of in another container after the sharps are used.

SUMMARY OF INVENTION

The present invention seeks to resolve a number of the problems which have been experienced in the prior art, as identified above. More specifically, the apparatus and method of this invention constitute an important advance in the art of containers, as evidenced by the following objects and advantages realized by the invention over the prior art.

One object of the present invention is to preclude handling of items being disposed of by personnel during insertion into the container, thereby precluding contact with previously disposed sharps or other medical materials.

Yet another object of the present invention is to provide for interchangeable use of a lid with a plurality of container bodies.

Another object of the present invention is to provide a self-closing flap over the container opening.

Additionally, it is an object of the present invention to provide a means for locking the lid of the container in a closed position to make it tamper resistant.

A further object of the present invention is to provide a means for removal and disposal of syringe needles.

The container must also be disposable and made of nontoxic and incineratable materials, whereas the container may be incinerated and/or disposed of at a disposal site.

Additional objects and advantages of the invention will be apparent from the description which follows, or may be learned by the practice of the invention.

Briefly summarized, the foregoing objects are achieved by a container assembly which is utilized for both the transport of new sharps and the disposal of contaminated or used sharps.

The preferred embodiment comprises a lid and container assembly. The lid is designed to be interchangeable with a variety of different sized containers. The lid is also designed to be temporarily secured to the container while transporting new medical instruments. When using the container for disposal purposes, the lid may be permanently secured to the container.

The opening of the lid is relatively restricted, thereby allowing for the receipt of contaminated medical instruments and preventing removal of previously disposed instruments in the associated container. The lid includes an area for placement of a contaminated article wherein a person may then dispose of the article without touching the article presently being disposed of as well as previously disposed articles. Moreover, the lid prevents further handling of used items by medical personnel subsequent to disposal. The invention may also comprise a single container wherein the lid and container are formed as one.

Non-medical items may be utilized with the inventive lid and container assembly. For example, batteries, industrial items, chemical items, cosmetics and computer software may be transported in a container incorporating the present invention and then disposed of in the same container. Household items such as chlorine bleach, lye, soap, phosphates, ammonia, vinegar and alcohol may also be transported and then disposed of in the same container.

When used with medical or chemical products, the container assembly may also contain an absorbent pad and chemical agents for neutralizing the items. In addition, the inventive container assembly may be used for transport and storage of agricultural items and automotive parts. Soiled automotive parts may later be safely disposed of in the same container. Other uses for the container include transport and disposal of environmentally unsafe products such as coal and oil.

These and other features of the present invention can be best understood from the following specification and drawings, of which the following is a brief description.

BRIEF DESCRIPTION OF DRAWINGS

Figure 1:
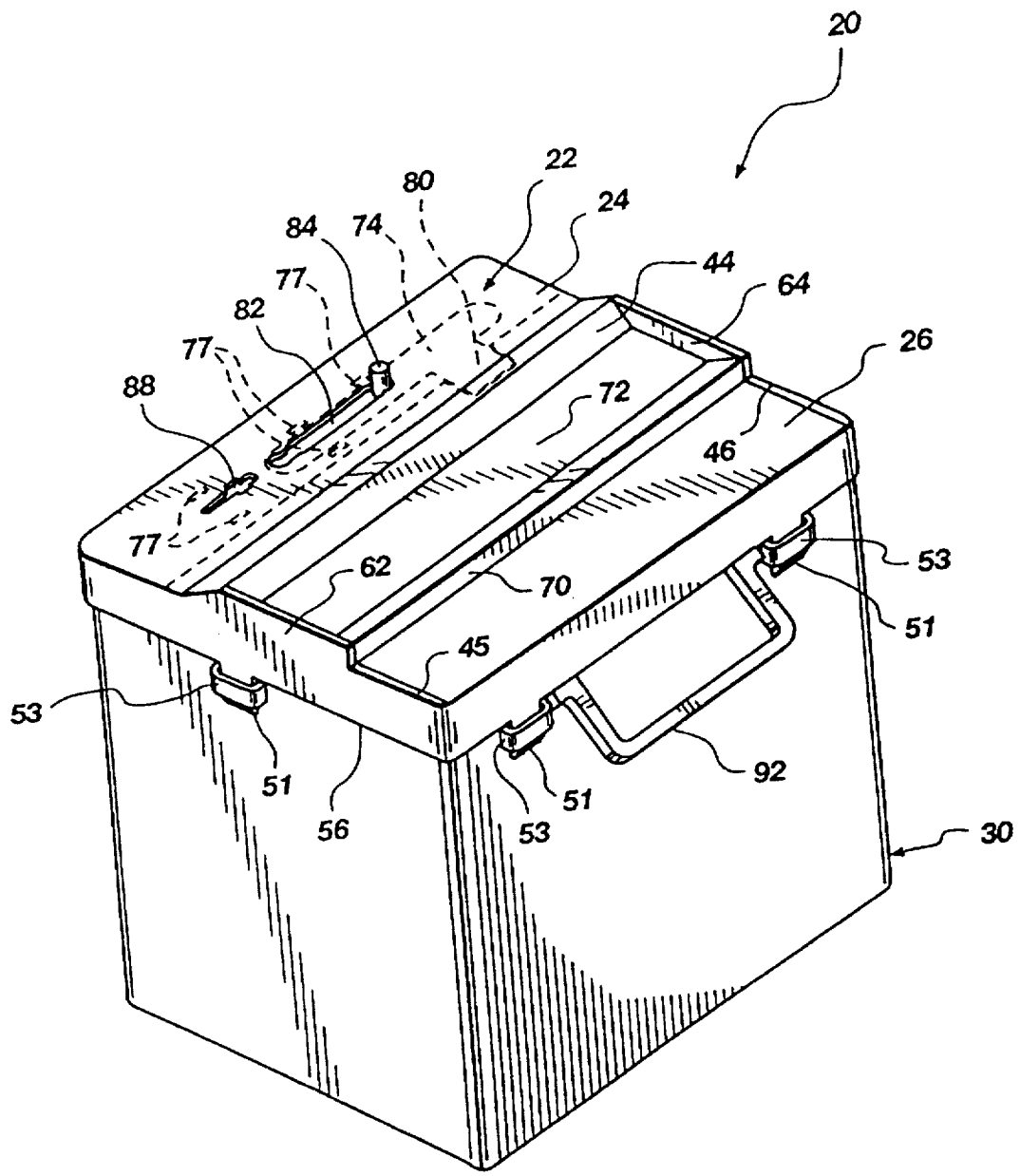
FIG. 1 is a perspective view showing the container assembly in a closed position.

In order to more fully understand the manner in which the above-recited advantages and objects of the invention are obtained, a more particular description of the invention will be rendered by reference to specific embodiments thereof which are illustrated in the appended drawings. Understanding that these drawings depict only typical embodiments of the invention and are therefore not to be considered limiting of its scope, the presently preferred embodiments and the presently understood best mode of the invention will be described with additional detail through use of the accompanying drawings in which:

FIG. 1 is a perspective view showing the container assembly in a closed position.

FIG. 2 is a perspective view showing the lid separate from the container.

Figure 3:
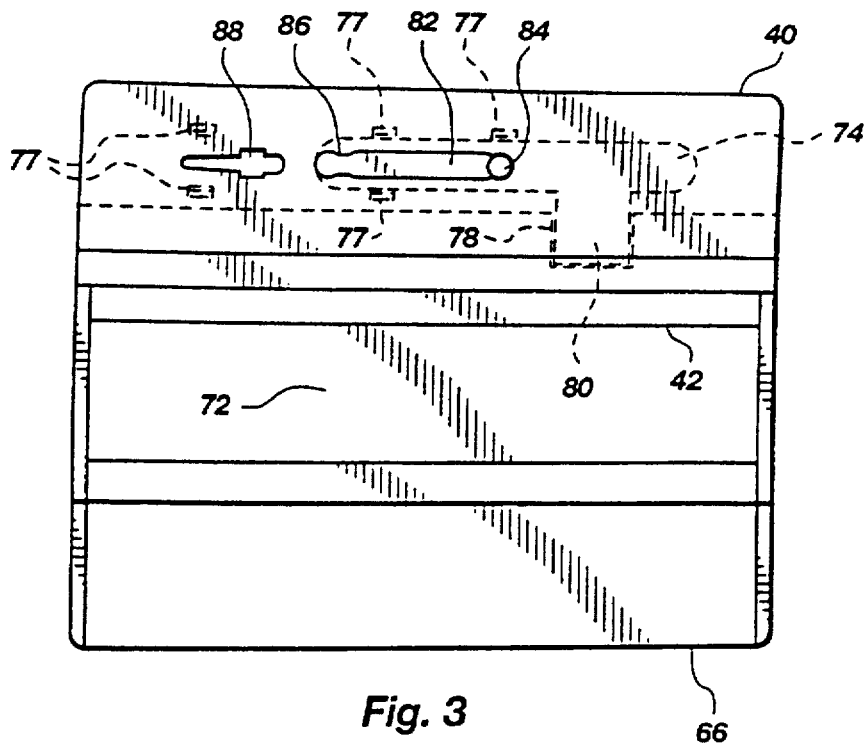
FIG. 3 is a top view of the container assembly in a closed position.

FIG. 3 is a top view of the container assembly in a closed position.

Figure 4:
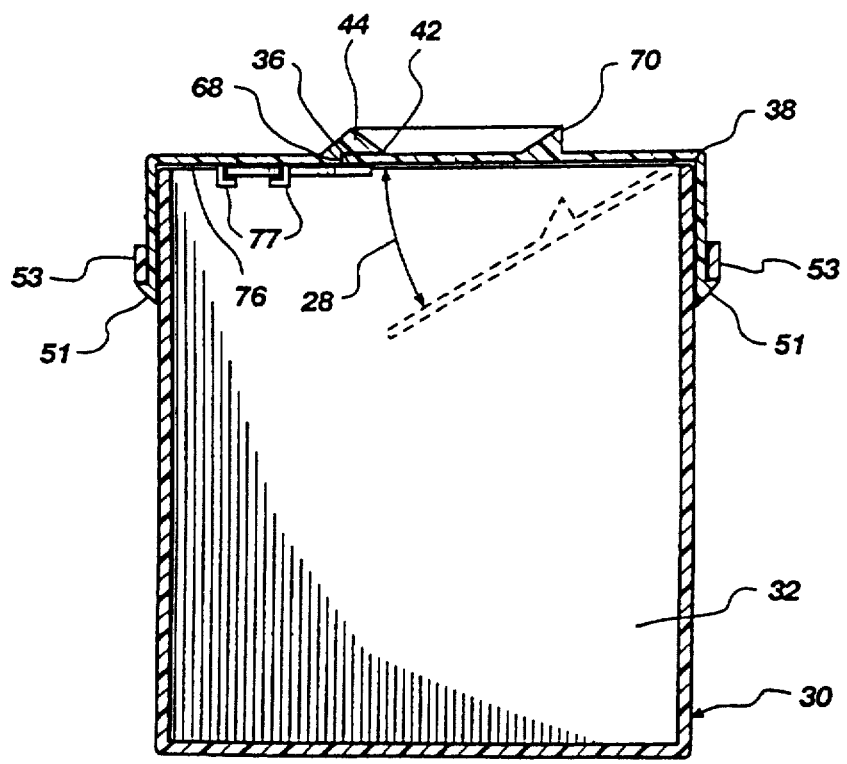
FIG. 4 is a cross-sectional view of the container assembly.

FIG. 4 is a cross-sectional view of the container assembly.

FIG. 5 is a perspective view showing the lid formed as part of the container assembly.

FIG. 6 is a perspective view showing an alternative means for securing the lid to the container by means of arrow tabs.

FIG. 7 is a perspective view showing a cylindrical container assembly.

FIG. 8 is a perspective view showing the lid formed as part of the cylindrical container body.

DETAILED DESCRIPTION OF THE PREFERRED EMBODIMENT

Reference is now made to the drawings, wherein like numerals are used to denote like elements throughout. The container assembly of the present invention, generally designated 20, comprises a lid body 22, a self-closing biased flap 26, an opening 28, and a container body 30. The container body 30 defines a volume 32 and includes an opening 34. Although FIGS. 1-6 illustrate a rectangular shaped volume 32, one skilled in the art will recognize that many other shapes fall within the purview of this invention. For example, the container assembly may be square, spherical or cylindrical in shape as shown in FIGS. 7 and 8. Of course, manufacturing concerns are important in determining the shape of the volume 32. In the preferred embodiment, the lid body 22 is separate from the container body 30. The lid body 22 is adapted to be used with a plurality of container bodies 30. This design feature facilitates the manufacturing ease in which a variety of multiple-sized containers are produced for use with a one-size-fits-all container lid. However, the lid body 22 may also be formed as part of the container body 30 as shown in FIGS. 5 and 8. Each of these elements, as well as many others, will be discussed in greater detail hereafter.

The lid 22 and container body 30 are preferably constructed of a semi-rigid plastic or similar material which is lightweight, non-toxic, incineratable, inexpensive, easily manufactured, and sturdy. Size considerations may dictate that the container body 30 further comprise ribs to enhance structural integrity.

The biased flap 26 includes a first end 66 and a second end 68 wherein the biasing feature is accomplished by a living hinge 38 at the first end 66. A living hinge refers to hinged material having memory, such that when it is forcibly bent, it returns to its original position. The hinged material is typically notched along the living hinge. The biasing may also be accomplished by a spring interposed between the biased flap 26 and the container body 30.

The container assembly 20 also comprises a cradling means for insertion of medical instruments and waste into the container body 30 through the opening 28, wherein the cradling means has a floor 72 disposed on the biased flap 26. The cradling means is defined by an area surrounded by enclosure walls. A first enclosure wall 70 extends outwardly from the container body 30. The biased flap 26 has a first side 45 and a second side 46, wherein the first enclosure wall 70 extends from the first side 45 to the second side 46 of the biased flap 26 and is located between the first end 66 and the second end 68 of the biased flap 26. The second enclosure wall is defined by a combination of enclosure walls 44, 62, and 64. The second enclosure wall extends outwardly on the container body opening 34 and is defined by the perimeter of the container body opening 34 abutting the second end 68 of the biased flap 26 and the first side 45 and second side 46 of the biased flap 26 between the first enclosure wall 70 and the second end 68 of the biased flap 26, such that a cradling means floor 72 is defined by the area enclosed by the first and second enclosure walls. One skilled in the art will recognize that the enclosure walls may be constituted in a number of combinations of securement to the lid body 22 or container body 30. For example, enclosure wall 62 and enclosure wall 64 may be formed with first enclosure wall 70 on the biased flap 26. Alternatively, first enclosure wall 70, enclosure wall 62, and enclosure wall 64 may be formed as one part with enclosure wall 44 on the container body 30. The cradling means may also comprise a recessed area in the biased flap 26. For example, the biased flap 26 may step inwardly such that the sides of the container body 30 act as enclosure walls.

The container assembly also comprises a stopping means for maintaining the biased flap 26 in a closed position. Preferably, the stopping means comprises a second flap 24 affixed to the container body 30 at the opening 34 and extending towards the biased flap 26 such that the second flap 24 overlies a portion 36 of the biased flap 26. The biased flap 26 is biased against the second flap 24 by use of a living hinge 38. In this manner, the opening 28 is normally closed. In this embodiment, the second flap 24 also includes a first and second end 40 and 42, respectively. The second end 42 of the second flap 24 includes an enclosure wall 44 protruding in a direction normal to the second flap 24. The stopping means may also comprise one or more tabs positioned at the container opening 34 and overlying a portion of the second end 68, first side 45, or second side 46 of the biased flap 26.

The lid 22 is attached to the container body 30 by an attaching or securing means. In the preferred embodiment, the attaching means comprises a plurality of tabs 47 located on the perimeter of the lid 22. Each tab 47 includes a distal end at which is disposed a protruding edge 51 for engagement with a corresponding female slot 53 located on the container. Once the tab 47 is fully inserted through the female slot 53, the protruding edge 51 locks the tabs in place. Alternatively, hinged pull tabs hingedly secured to the lid may be utilized, as shown in FIG. 6. In this embodiment, each pull tab includes a female end 48 of an arrow lock for engagement with a corresponding male end 50 located on the container body 30. One skilled in the art will recognize that these methods serve as attaching or securing means, although other methods may be used which are equivalent and thus fall within the scope of this invention. For example, the securing means may comprise a tongue and groove configuration or other locking tab configurations typically found in lid and container assemblies. The attaching means may be continuous or intermittent around the perimeter of the container opening 34 and lid body 22.

In the preferred embodiment, the tabs 47 and slots 53 are not positioned symmetrically about the perimeter of the lid 22 so that the lid 22 can be rotated one-hundred and eighty degrees to avoid permanent securement during shipment of new medical instruments. Once the new medical instruments are removed, the lid 22 is then oriented for engagement of the tabs 47 into the corresponding slots 53 for permanent securement while using the container 30 for disposal purposes. Alternative securing means would similarly be misaligned for temporary and later permanent securement.

The container assembly 20 further comprises a means for locking the biased flap 26 in a closed position. In the preferred embodiment the locking means comprises an elongated plate 74 slidably mounted to the underside 76 of the second flap 24. The plate 74 slides along tracks 77. The second end 68 of the biased flap 26 includes a notch 78 which is configured to match the outline of a tab 80 extending outwardly from the elongated plate 74. The profile of the tab 80 is slightly smaller than the notch 78 so that the biased flap 26 may be freely depressed while the locking means is in the open position. The closed position is defined by the plate 74 positioned such that the tab 80 is located adjacent to the notch 78, thereby preventing depression of the biased flap 26, as shown in FIG. 2. The second flap 24 also includes a slit 82 for slidable translation of a knob 84 attached to the plate 74 for positioning in an open, closed, or permanently closed position. The permanently closed position is defined by the knob 84 extended past a necked section 86 in the slit 82 of slightly smaller width than the knob 84.

Additionally, a strip of adhesive tape may be used as a method of sealing the second and biased flaps 24 and 26, respectively, together.

The container assembly 20 further comprises a means for extracting needles from a syringe. In the preferred embodiment, a tapered opening 88 located on the second flap 24 is used for extracting needles from a syringe. The needle is removed from the syringe by slidably engaging the needle base in the narrowest portion of the tapered opening 88 allowed and then twisting the syringe such that the threaded needle base dislodges from the syringe and falls into the volume 32. The means for extracting needles may also comprise multiple-sized openings, either separate or in series, which correspond to the geometry of the base of the needle such that when the needle base is inserted through the opening, the sides of the opening lockably fix the needle base for removal of the needle and insertion into the container assembly 20.

The container assembly 20 is also adapted to be mounted to a wall surface by means of a bracket 90 which is attached to the container body 30 and a corresponding adapter rigidly secured to the wall surface. For example, this adaptation of the container assembly 20 is advantageous in a hospital setting whereby a number of medical personnel may utilize the invention in a convenient and centralized locale.

The container assembly 20 for transporting and disposing of medical instruments is used as follows. When the container assembly 20 is used for transporting new medical instruments, the instruments are placed inside the container volume 32 with the lid 22 temporarily secured by orienting the tabs 47 and slots 53 in the misaligned position. When the container assembly 20 is used for disposal of used medical instruments, the lid 22 is permanently secured to the container 30 by orienting the tabs 47 and corresponding slots 53 in the aligned position such that the tabs 47 slide through the slots 53 and the protruding edges 51 lock the tabs 47 in place. The medical instruments desired to be disposed of are inserted into the container assembly 20 by placing the instruments on the floor 72 of the cradling means defined by the enclosure walls 44, 62, 64 and first enclosure wall 70, and then pressing downward on the biased flap in an area adjacent to the cradling means, thereby allowing the instruments to fall inside the volume 32 without contacting the instruments disposed of. Once the instruments are inserted, the danger of the instruments accidentally falling out or injuring someone are virtually eliminated. The lid 22 body of the container assembly 20 is then locked by sliding the knob 84 into the permanently locked position prior to transporting. A handle 92 attached to the container assembly 20 further facilitates its transportability.

In summary, the method and apparatus disclosed herein is a significant improvement from the present state of the containers for the sealed transport and disposal of medical instruments.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A container for use in transport and disposal of medical instruments, comprising:
   a container body having an opening;
   a self-closing biased flap connected to the container body for covering the opening;
   a cradling means for insertion of medical instruments and waste into the container body through the opening, said cradling means comprising:

a first enclosure wall on the biased flap extending outwardly from the container body, said biased flap having a first side, a second side, a first end, and a second end, said first enclosure wall extending from the first side to the second side and located between the first end and second end of the biased flap;

a second enclosure wall on the container body opening extending outwardly and defined by the container body opening abutting the second end of the biased flap and the first side and second side of the biased flap between the first enclosure wall and second end of the biased flap; and a floor defined by an area on the biased flap enclosed by the first enclosure wall and the second enclosure wall.

2. A device as defined in claim 1, further comprising a stopping means for maintaining the biased flap in a closed position.

3. A device as defined in claim 2, further comprising a means for locking the biased flap in the closed position.

4. A device as defined in claim 3, wherein said stopping means comprises a second flap affixed to the container body at the opening and extending towards the biased flap, said second flap overlying a portion of the biased flap, said second flap including an underside and the biased flap having a second end extending towards the second flap, said second end of the biased flap including a notch, and the locking means comprising an elongated plate with an outwardly extending tab of a shape corresponding to the notch, said plate slidably mounted to the underside of the second flap, and the closed position defined by the plate positioned such that the tab is located adjacent to the notch on the biased flap, thereby preventing depression of the biased flap.

5. A device as defined in claim 4, wherein the second flap includes a slit for slidable translation of a knob adapted to be attached to the plate for positioning in an open, closed, or permanently closed position.

6. A device as defined in claim 5, wherein the open position is defined by the tab in alignment with the notch in the biased flap such that the biased flap may be depressed without interference of the tab.

7. A device as defined in claim 5, wherein the slit includes a necked section of slightly smaller width than the knob and the permanently closed position is defined by the knob extended beyond the necked section in the slit.

8. A device as defined in claim 3, further comprising means for extracting needles from a syringe.

9. A container for use in transport and disposal of medical instruments, comprising:

a container body having an opening;

a self-closing biased flap connected to the container body for covering the opening;

a cradling means for insertion of medical instruments and waste into the container body through the opening, said cradling means comprising:

a first enclosure wall on the biased flap extending outwardly from the container body, said biased flap having a first side, a second side, a first end, and a second end, said first enclosure wall extending from the first side to the second side and located between the first end and second end of the biased flap and also extending along the first side and second side of the biased flap from the first enclosure wall to the second end of the biased flap;

a second enclosure wall on the container body opening extending outwardly and defined by the container body opening abutting the second end of the biased flap; and a floor defined by an area on the biased flap enclosed by the first enclosure wall and the second enclosure wall.

10. A device as defined in claim 9, further comprising a stopping means for maintaining the biased flap in a closed position.

11. A device as defined in claim 10, further comprising a means for locking the biased flap in the closed position.

12. A device as defined in claim 11, further comprising means for extracting needles from a syringe.

13. A device as defined in claim 11, wherein said stopping means comprises a second flap affixed to the container body at the opening and extending towards the biased flap, said second flap overlying a portion of the biased flap, said second flap including an underside and the biased flap having a second end extending towards the second flap, said second end of the biased flap including a notch, and the locking means comprising an elongated plate with an outwardly extending tab of a shape corresponding to the notch, said plate slidably mounted to the underside of the second flap, and the closed position defined by the plate positioned such that the tab is located adjacent to the notch on the biased flap, thereby preventing depression of the biased flap.

14. A device as defined in claim 13, wherein the second flap includes a slit for slidable translation of a knob adapted to be attached to the plate for positioning in an open, closed, or permanently closed position.

15. A device as defined in claim 14, wherein the open position is defined by the tab in alignment with the notch in the biased flap such that the biased flap may be depressed without interference of the tab.

16. A device as defined in claim 14, wherein the slit includes a necked section of slightly smaller width than the knob and the permanently closed position is defined by the knob extended beyond the necked section in the slit.

17. A lid which attaches to containers for transport and disposal of medical instruments, comprising:

a lid body for enclosing a volume within a container, said lid body having an opening;

a self-closing biased flap connected to the lid body for covering the opening;

means for attaching said lid body to said container; and cradling means for insertion of medical instruments and waste through the opening, said cradling means comprising:

a first enclosure wall on the biased flap extending outwardly from the lid body, said biased flap having a first side, a second side, a first end, and a second end, said first enclosure wall extending from the first side to the second side and located between the first end and second end of the biased flap;

a second enclosure wall on the lid body opening extending outwardly and defined by the lid body opening abutting the second end of the biased flap and the first side and second side of the biased flap between the first enclosure wall and second end of the biased flap; and a floor defined by an area on the biased flap enclosed by the first enclosure wall and the second enclosure wall.

18. A device as defined in claim 17, further comprising a stopping means for maintaining the biased flap in a closed position.

19. A device as defined in claim 18, further comprising means for locking the biased flap in the closed position.

20. A device as defined in claim 19, wherein said stopping means comprises a second flap affixed to the container body at the opening and extending towards the biased flap, said second flap overlying a portion of the biased flap, said second flap including an underside and the biased flap having a second end extending towards the second flap, said second end of the biased flap including a notch, and the locking means comprising an elongated plate with an outwardly extending tab of a shape corresponding to the notch, said plate slidably mounted to the underside of the second flap, and the closed position defined by the plate positioned such that the tab is located adjacent to the notch on the biased flap, thereby preventing depression of the biased flap.

21. A device as defined in claim 20, wherein the second flap includes a slit for slidable translation of a knob adapted to be attached to the plate for positioning in an open, closed, or permanently closed position.

22. A device as defined in claim 21, wherein the open position is defined by the tab in alignment with the notch in the biased flap such that the biased flap may be depressed without interference of the tab.

23. A device as defined in claim 21, wherein the slit includes a necked section of slightly smaller width than the knob and the permanently closed position is defined by the knob extended beyond the necked section in the slit.

24. A device as defined in claim 19, further comprising means for extracting needles from a syringe.

25. A lid which attaches to containers for transport and disposal of medical instruments, comprising:
a lid body for enclosing a volume within a container, said lid body having an opening;
a self-closing biased flap connected to the lid body for covering the opening;
means for attaching said lid body to said container; and
cradling means for insertion of medical instruments and waste through the opening, said cradling means comprising:
a first enclosure wall on the biased flap extending outwardly from the lid body, said biased flap having a first side, a second side, a first end, and a second end, said first enclosure wall extending from the first side to the second side and located between the first end and second end of the biased flap and also extending along the first side and second side of the biased flap from the first enclosure wall to the second end of the biased flap;
a second enclosure wall on the lid body opening extending outwardly and defined by the lid body opening abutting the second end of the biased flap; and
a floor defined by an area on the biased flap enclosed by the first enclosure wall and the second enclosure wall.

26. A device as defined in claim 25, further comprising a stopping means for maintaining the biased flap in a closed position.

27. A device as defined in claim 26, further comprising means for locking the biased flap in the closed position.

28. A device as defined in claim 27, further comprising means for extracting needles from a syringe.

29. A device as defined in claim 27, wherein said stopping means comprises a second flap affixed to the container body at the opening and extending towards the biased flap, said second flap overlying a portion of the biased flap, said second flap including an underside and the biased flap having a second end extending towards the second flap, said second end of the biased flap including a notch, and the locking means comprising an elongated plate with an outwardly extending tab of a shape corresponding to the notch, said plate slidably mounted to the underside of the second flap, and the closed position defined by the plate positioned such that the tab is located adjacent to the notch on the biased flap, thereby preventing depression of the biased flap.

30. A device as defined in claim 29, wherein the second flap includes a slit for slidable translation of a knob adapted to be attached to the plate for positioning in an open, closed, or permanently closed position.

31. A device as defined in claim 30, wherein the open position is defined by the tab in alignment with the notch in the biased flap such that the biased flap may be depressed without interference of the tab.

32. A device as defined in claim 30, wherein the slit includes a necked section of slightly smaller width than the knob and the permanently closed position is defined by the knob extended beyond the necked section in the slit.

* * * * *